(12) United States Patent
Imahori

(10) Patent No.: US 8,846,905 B2
(45) Date of Patent: Sep. 30, 2014

(54) PORPHYRIN COMPLEX AND USE THEREOF

(75) Inventor: Hiroshi Imahori, Kyoto (JP)

(73) Assignee: Kyoto University, Kyoto-shi (JP)

( * ) Notice: Subject to any disclaimer, the term of this patent is extended or adjusted under 35 U.S.C. 154(b) by 11 days.

(21) Appl. No.: 13/583,023

(22) PCT Filed: Mar. 9, 2011

(86) PCT No.: PCT/JP2011/055449
§ 371 (c)(1),
(2), (4) Date: Oct. 23, 2012

(87) PCT Pub. No.: WO2011/111725
PCT Pub. Date: Sep. 15, 2011

(65) Prior Publication Data
US 2013/0042916 A1    Feb. 21, 2013

(30) Foreign Application Priority Data

Mar. 10, 2010 (JP) ................. 2010-053679

(51) Int. Cl.
*C07D 487/22* (2006.01)
*C09B 47/04* (2006.01)
*H01M 14/00* (2006.01)

(52) U.S. Cl.
CPC ........... *H01M 14/005* (2013.01); *C09B 47/045* (2013.01); *C07D 487/22* (2013.01)
USPC ...................................................... 540/145

(58) Field of Classification Search
USPC ...................................................... 540/145
See application file for complete search history.

(56) References Cited

U.S. PATENT DOCUMENTS

2006/0030718 A1    2/2006    Zhang

FOREIGN PATENT DOCUMENTS

| JP | 2008-274082 A1 | 11/2008 |
|---|---|---|
| JP | 2009-280702 A1 | 12/2009 |

OTHER PUBLICATIONS

Effects of meso-Diarylamino Group of Porphyrins as Sensitizers in Dye-Sensitized Solar Cells on Optical, Electrochemical, and Photovoltaic Properties, Imahori et al. J. Phys. Chem. C, 2010, 114 (23), pp. 10656-10665.*
H. Imahori, et al.; "Large pi-Aromatic Molecules as Potential Sensitizers for Highly Efficient Dye-Sensitized Solar Cells;" Accounts of Chemical Research; vol. 42; No. 11; Nov. 2009; pp. 1809-1818.
Y. Chen, et al.; "Facile and Efficient Synthesis of meso-Arylamino- and Alkylamino-Substituted Porphyrins via Palladium-Catalyzed Amination;" Journal of Organic Chemistry; vol. 68; No. 11; 2003; pp. 4432-4438.
H. Lu, et al.; "Control of Dye Aggregation and Electron Injection for Highly Efficient Porphyrin Sensitizers Adsorbed on Semiconductor Films with Varying Ratios of Coadsorbate;" Journal of Physical Chemistry C; vol. 113; No. 49; 2009; pp. 20990-20997.
A.V. Barzykin, et al.; "Mechanism of Molecular Control of Recombination Dynamics in Dye-Sensitized Nanocrystalline Semiconductor Films;" Journal of Physical Chemistry B; vol. 108; No. 24; 2004; pp. 8385-8389.
International Search Report for International Application No. PCT/JP2011/055449 dated May 24, 2011.

* cited by examiner

*Primary Examiner* — Brian McDowell
(74) *Attorney, Agent, or Firm* — Kratz, Quintos & Hanson, LLP

(57) ABSTRACT

An object of the present invention is to provide a novel porphyrin complex having excellent light collection characteristics and a dye-sensitized solar cell using the porphyrin complex as a sensitizing dye. The porphyrin complex of the present invention as a means for achieving the object is characterized by comprising a porphyrin derivative and a metal atom. The porphyrin derivative has a carboxyaryl group, which is optionally substituted on the aryl ring, attached to at least one of four meso positions of a porphyrin ring optionally substituted at the β-position and also has a diarylamino group, which is optionally substituted on one or both of the aryl rings, attached to at least either of a meso position adjacent thereto and a meso position opposite thereto.

5 Claims, 5 Drawing Sheets

PORPHYRIN COMPLEX AND USE THEREFOR

TECHNICAL FIELD

The present invention relates to a novel porphyrin complex and the use thereof. More specifically, the present invention relates to a complex compound of a porphyrin derivative having carboxyaryl and diarylamino groups attached to meso positions thereof with a metal atom, and also to a dye-sensitized solar cell using the complex compound as a sensitizing dye.

BACKGROUND ART

As is widely known, solar cells that can convert the energy of light into electricity have been attracting much attention as a future clean energy source. In particular, dye-sensitized solar cells using a sensitizing dye are easy to produce, and also such cells can be provided with colorability, flexibility, etc. In this respect, they have different features from solar cells using silicon or an inorganic compound, and various intensive researches and developments have been made. As a result, some of solar cells using a sensitizing dye made of a Ru complex (Ru-based dye), for example, have achieved energy conversion efficiency (II) of more than 10%, and are expected to be put into practical use (Nonpatent Document 1). However, a Ru-based dye uses an expensive, rare metal element Ru, and thus has problems of high production cost and limited resources. Accordingly, there is a demand for the development of a sensitizing dye which is lower in cost and whose resources are less limited.

It is a well known fact to those skilled in the art that porphyrin is a compound useful as a sensitizing dye because of the ease of molecular design, the high extinction coefficient, and the low cost of synthesis. In the case where porphyrin is used as a sensitizing dye, its molecular structure basically includes a porphyrin ring and an anchor unit introduced therein (e.g., in a porous layer of particles of a metal oxide such as $TiO_2$ formed on the surface of a transparent electrode, a unit that functions to allow the sensitizing dye to be adsorbed to the surface of each metal oxide particles). As such a porphyrin derivative, for example, 5-(4-carboxyphenyl)-10,15,20-tetrakis(2,4,6-trimethylphenyl)porphyrinatozinc(II) having a carboxyphenyl group as an anchor unit at a meso position (abbreviated as ZnP), as represented by the following chemical structure formula, is known. However, this compound has poor ability to collect light at a wavelength near 500 nm and also at a wavelength of 600 nm or more (Nonpatent Document 2). As a method for improving the insufficient light collection characteristics of such a porphyrin derivative, for example, a method in which a further substituent is introduced into the porphyrin ring for the purpose of optimizing the molecular structure is mentioned. However, its effectiveness has not yet been completely proven.

[Chemical Formula 1]

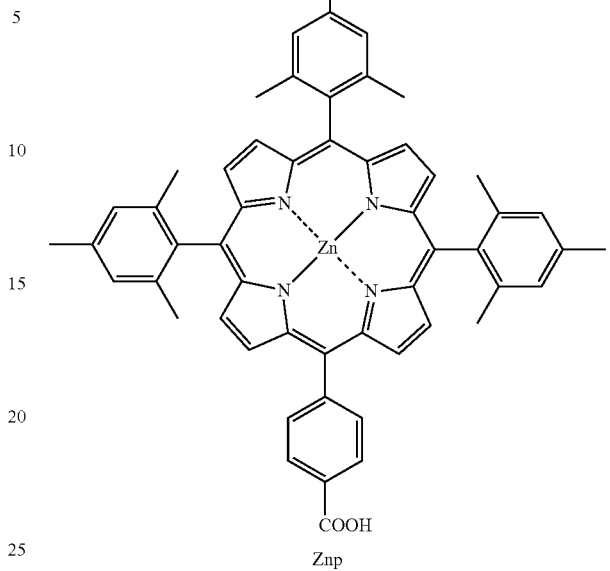

Znp

PRIOR ART DOCUMENTS

Nonpatent Documents

Nonpatent Document 1: Graetzel, M. et al., J. Am. Chem. Soc., 2005, 127, 16835
Nonpatent Document 2: Imahori, H. et al., Acc. Chem. Res., 2009, 42, 1809

SUMMARY OF THE INVENTION

Problems that the Invention is to Solve

Thus, an object of the present invention is to provide a novel porphyrin complex having excellent light collection characteristics and a dye-sensitized solar cell using the porphyrin complex as a sensitizing dye.

Means for Solving the Problems

In light of the above points, the present inventor conducted extensive research. As a result, he has found that in a porphyrin ring having a carboxyaryl group such as a carboxyphenyl group attached to a meso position thereof, when a diarylamino group is introduced into another meso position, light collection characteristics can be improved.

A porphyrin complex of the present invention accomplished based on the above findings is, as defined in a first embodiment, characterized by comprising a porphyrin derivative and a metal atom,
the porphyrin derivative having:
a carboxyaryl group, which is optionally substituted on the aryl ring, attached to at least one of four meso positions of a porphyrin ring optionally substituted at the β-position; and
a diarylamino group, which is optionally substituted on one or both of the aryl rings, attached to at least either of a meso position adjacent thereto and a meso position opposite thereto.

A porphyrin complex according to a second embodiment is characterized in that in the porphyrin complex according to the first embodiment, the porphyrin complex is represented by the following general formula (1).

[Chemical Formula 2]

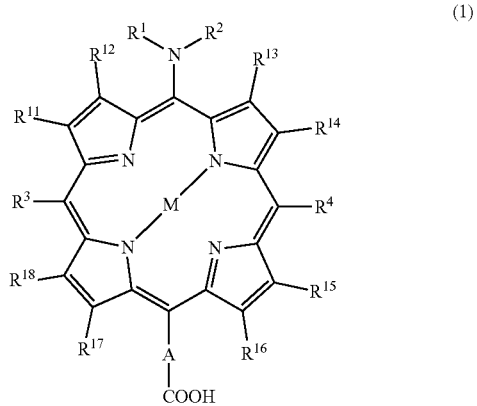

(1)

[In the formula, A represents an optionally substituted arylene group; $R^1$ and $R^2$ may be the same or different and each represent an optionally substituted aryl group; $R^3$ and $R^4$ may be the same or different and each represent a diarylamino group optionally substituted on one or both of the aryl rings, a carboxyaryl group optionally substituted on the aryl ring, an optionally substituted aryl group, or an arylethynyl group optionally substituted on the aryl ring; $R^{11}$ to $R^{18}$ may be the same or different and each represent a hydrogen atom, an optionally substituted alkyl group, an optionally substituted aryl group, an arylethynyl group optionally substituted on the aryl ring, or a halogen atom; and M represents a metal atom.]

A porphyrin complex according to a third embodiment is characterized in that in the porphyrin complex according to the first embodiment, the porphyrin complex is represented by the following general formula (2).

[Chemical Formula 3]

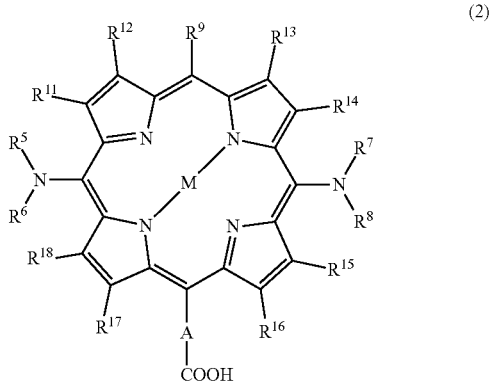

(2)

[In the formula, A, $R^{11}$ to $R^{18}$, and M are as defined above; $R^5$, $R^6$, $R^7$, and $R^8$ may be the same or different and each represent an optionally substituted aryl group; and $R^9$ represents an optionally substituted aryl group or an arylethynyl group optionally substituted on the aryl ring.]

A porphyrin complex according to a fourth embodiment is characterized in that in the porphyrin complex according to the first embodiment, the number of diarylamino groups attached is 2 or more.

A porphyrin complex according to a fifth embodiment is characterized in that in the porphyrin complex according to any one of the first to fourth embodiments, the metal atom is Zn, Cu, Ti, Ni, Fe, or Mg.

A dye-sensitized solar cell of the present invention is, as defined in a sixth embodiment, characterized by comprising a transparent electrode having on a surface thereof a porous layer formed by the adsorption of the porphyrin complex according to any one of the first to fifth embodiments as a sensitizing dye on metal oxide particles.

Effect of the Invention

The present invention enables the provision of a novel porphyrin complex having excellent light collection characteristics and a dye-sensitized solar cell using the porphyrin complex as a sensitizing dye.

MODE FOR CARRYING OUT THE INVENTION

Figure 1:
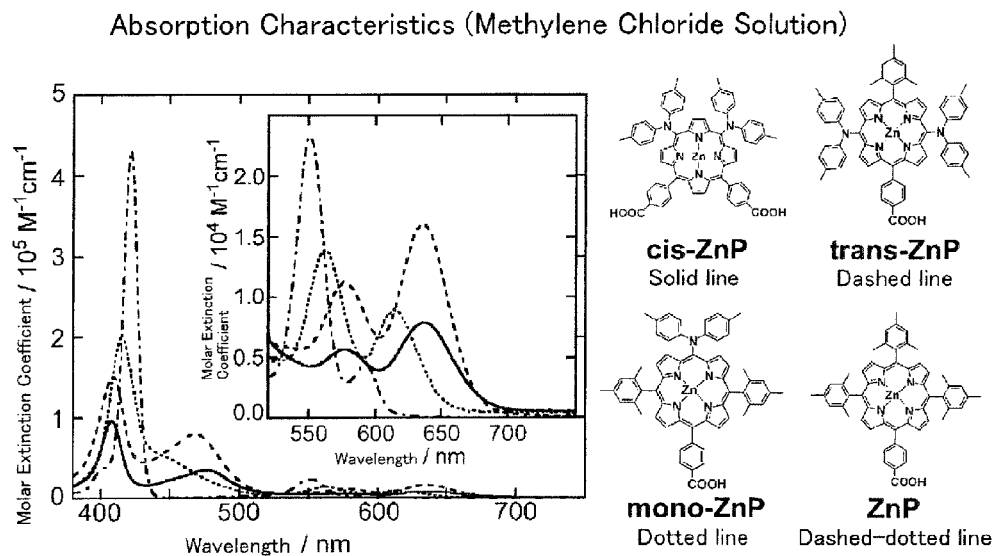
FIG. 1: Spectra showing the results of the evaluation of the light absorption characteristics of porphyrin complexes of the present invention (cis-ZnP, trans-ZnP, and mono-ZnP) in the Examples.

The porphyrin complex of the present invention is characterized by containing a porphyrin derivative and a metal atom. The porphyrin derivative has a carboxyaryl group, which is optionally substituted on the aryl ring, attached to at least one of four meso positions of a porphyrin ring optionally substituted at the β-position and also has a diarylamino group, which is optionally substituted on one or both of the aryl rings, attached to at least either of a meso position adjacent thereto and a meso position opposite thereto. In a porphyrin ring having a carboxyaryl group such as a carboxyphenyl group attached to a meso position thereof, when a diarylamino group is introduced into another meso position, light collection characteristics can be improved. The effectiveness increases with an increase in the number of diarylamino groups introduced.

As a specific example of the porphyrin complex of the present invention, a porphyrin complex represented by the following general formula (1) at least having a diarylamino group attached to a meso position of the porphyrin ring, which is opposite to a meso position to which a carboxyaryl group is attached, is mentioned.

[Chemical Formula 4]

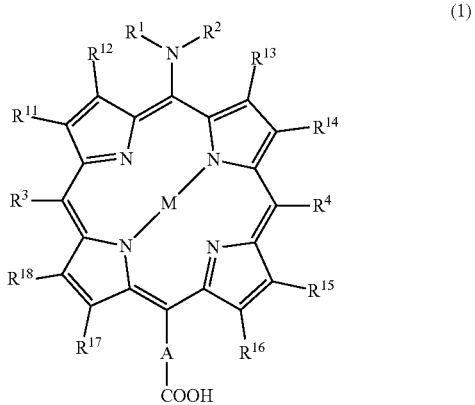

(1)

[In the formula, A represents an optionally substituted arylene group; $R^1$ and $R^2$ may be the same or different and each represent an optionally substituted aryl group; $R^3$ and $R^4$ may be the same or different and each represent a diarylamino group optionally substituted on one or both of the aryl rings, a carboxyaryl group optionally substituted on the aryl ring, an optionally substituted aryl group, or an arylethynyl group optionally substituted on the aryl ring; $R^{11}$ to $R^{18}$ may be the same or different and each represent a hydrogen atom, an optionally substituted alkyl group, an optionally substituted aryl group, an arylethynyl group optionally substituted on the aryl ring, or a halogen atom; and M represents a metal atom.]

As another specific example of the porphyrin complex of the present invention, a porphyrin complex represented by the following general formula (2) having diarylamino groups attached to two meso positions of the porphyrin ring, which are adjacent to a meso position to which a carboxyaryl group is attached, is mentioned.

[Chemical Formula 5]

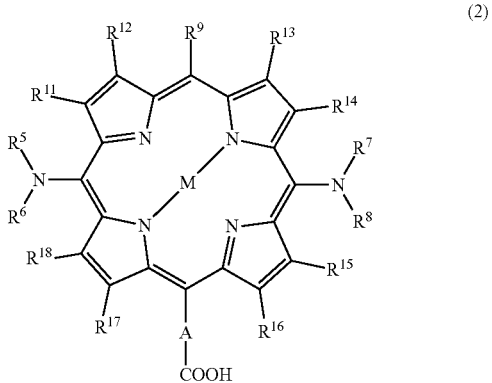

(2)

[In the formula, A, $R^{11}$ to $R^{18}$, and M are as defined above; $R^5$, $R^6$, $R^7$, and $R^8$ may be the same or different and each represent an optionally substituted aryl group; and $R^9$ represents an optionally substituted aryl group or an arylethynyl group optionally substituted on the aryl ring.]

In the porphyrin complex represented by the above general formula (1) and the porphyrin complex represented by the above general formula (2), examples of arylene groups for A include a phenylene group and a naphthylene group. Examples of aryl groups for $R^1$ to $R^9$ and $R^{11}$ to $R^{18}$, aryl moieties in diarylamino groups for $R^3$ and $R^4$, aryl moieties in carboxyaryl groups for $R^3$ and $R^4$, and aryl moieties in arylethynyl groups for $R^3$, $R^4$, $R^9$, and $R^{11}$ to $R^{18}$ include a phenyl group and a naphthyl group. Alkyl groups for $R^{11}$ to $R^{18}$ may be $C_{1-20}$ linear, branched, or cyclic alkyl groups, for example. Specific examples thereof include a methyl group, an ethyl group, a propyl group, an isopropyl group, a butyl group, an isobutyl group, a sec-butyl group, a tert-butyl group, a pentyl group, an isopentyl group, a hexyl group, a cyclohexyl group, an octyl group, and a decyl group. Examples of halogen atoms for $R^{11}$ to $R^{18}$ include a fluorine atom, a chlorine atom, a bromine atom, and an iodine atom.

Examples of optional substituents on arylene groups for A, optional substituents on aryl groups for $R^1$ to $R^9$ and $R^{11}$ to $R^{18}$, optional substituents on aryl moieties in diarylamino groups for $R^3$ and $R^4$, optional substituents on aryl moieties in carboxyaryl groups for $R^3$ and $R^4$, optional substituents on aryl moieties in arylethynyl groups for $R^3$, $R^4$, $R^9$, and $R^{11}$ to $R^{18}$, and optional substituents on alkyl groups for $R^{11}$ to $R^{18}$ include halogen atoms such as a fluorine atom, a chlorine atom, a bromine atom, and an iodine atom, a hydroxy group, a nitro group, an amino group, a mono(lower alkyl)amino group, a di(lower alkyl)amino group, a lower alkylcarbonyl group, a lower alkoxycarbonyl group, a lower alkoxy group, a formyl group, a cyano group, a carboxy group, a carbonyl group, a carbamoyl group, a lower alkylcarbamoyl group, a lower alkylsulfonyl group, an arylsulfonyl group, a lower alkoxysulfonyl group, a sulfamoyl group, a lower alkylsulfamoyl group, a sulfanyl group, a sulfino group, a sulfo group, a di(lower alkyl)phosphoryl group, a diarylphosphoryl group, a di(lower alkoxy)phosphoryl group, a diaminophosphoryl group, $C_{1-20}$ linear, branched, or cyclic alkyl groups, for example, optionally having these substituents, and aryl and heteroaryl groups optionally having these substituents. The substituent is optionally protected with a known protective group. The term "lower" means that the number of carbon atoms is 1 to 6. Incidentally, the number of substituents is usually 1 to 3. In the case where the number of substituents is 2 or more, the two or more substituents may be the same or different.

Metal atoms for M are not particularly limited as long as they can be coordinated to a porphyrin ring. Preferred examples thereof include Zn, Cu, Ti, Ni, Fe, and Mg.

Specific examples of porphyrin complexes represented by the above general formula (1) include 5,10-bis(4-carboxyphenyl)-15,20-bis[N,N-bis(4-methylphenyl)amino]porphyrinatozinc(II) (abbreviated as cis-ZnP), 5-(4-carboxyphenyl)-10,20-bis(2,4,6-trimethylphenyl)-15[N,N-bis(4-methylphenyl)amino]porphyrinatozinc(II) (abbreviated as mono-ZnP), and 5-(4-carboxyphenyl)-10-(2,4,6-trimethylphenyl)-15,20-[N,N-(4-methylphenyl)amino]porphyrinatozinc(II) (abbreviated as bis-ZnP) represented by the following chemical structure formulae. In addition, specific examples of porphyrin complexes represented by the above general formula (2) include 5-(4-carboxyphenyl)-10,20-bis[N,N-bis(4-methylphenyl)amino]-15-(2,4,6-trimethylphenyl)porphyrinatozinc(II) (abbreviated as trans-ZnP) represented by the following chemical structure formula. Cis-ZnP, trans-ZnP, and bis-ZnP are compounds having two diarylamino groups attached to the porphyrin ring, and mono-ZnP is a compound having one diarylamino group attached to the porphyrin ring. These compounds can be synthesized through the formation of a porphyrin skeleton having a carboxyaryl group at a meso position (see, if necessary, e.g., Taniguchi, S. et al., Tetrahedron, 2001, 57, 2103; Cozzi, P. G. et al., ChemSusChem, 2009, 2, 218; Lee, C.-H. et al., Tetrahedron. Lett., 2000, 41, 4609; etc.), the formation of a complex by the coordination of a metal atom to the porphyrin ring, and the introduction of an amine compound into a meso position of the porphyrin ring using a trivalent iodine reagent, such as iodobenzene diacetate (PIDA), and a sodium salt of chloroauric acid or the like (see, if necessary, e.g., Shen, D.-M. et al., J. Org. Chem., 2009, 74, 206; etc.).

[Chemical Formula 6]

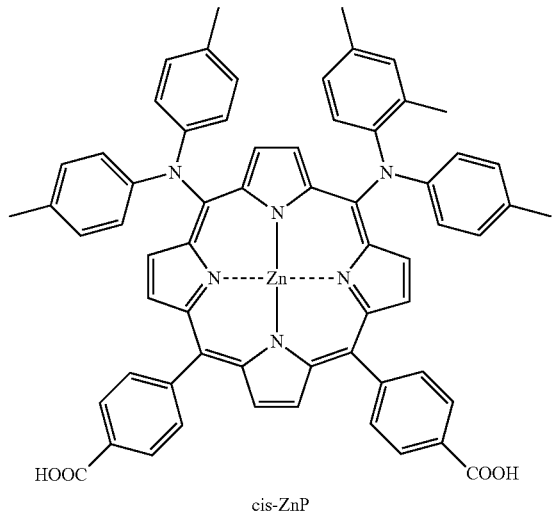

cis-ZnP

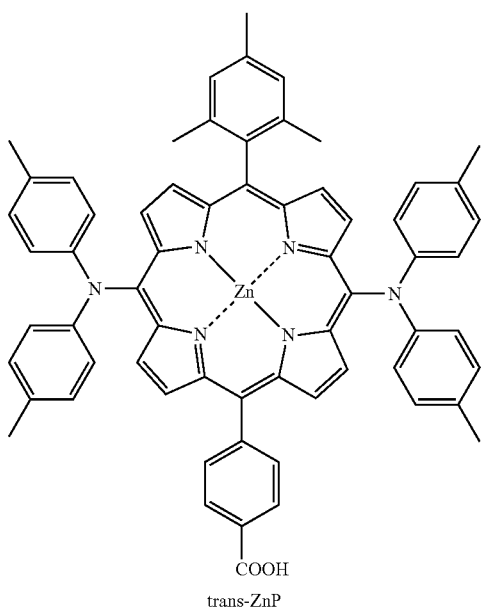

trans-ZnP

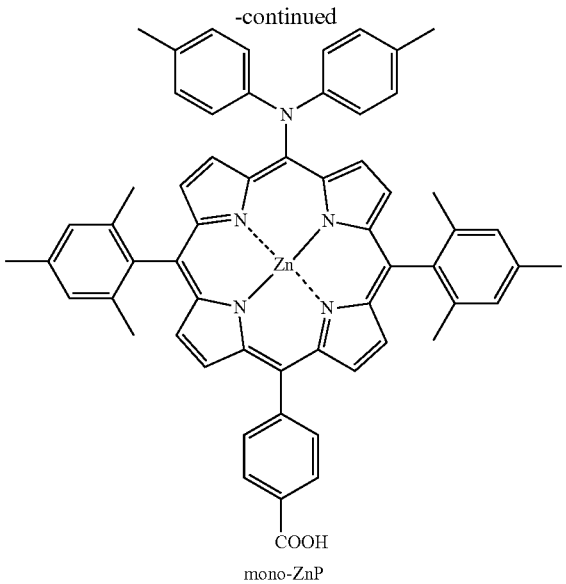

mono-ZnP

[Chemical Formula 7]

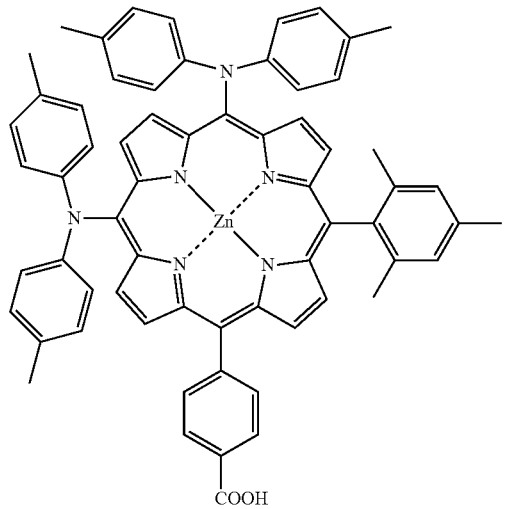

bis-ZnP

In a porous layer of particles of a metal oxide formed on the surface of a transparent electrode in a dye-sensitized solar cell, for example, the porphyrin complex of the present invention can be used as a sensitizing dye to be adsorbed to the surface of each metal oxide particles. A dye-sensitized solar cell usually includes, for example, a transparent electrode having formed on the surface thereof a porous layer having a sensitizing dye adsorbed therein, a counter electrode facing the transparent electrode, and an electrolyte placed between the transparent electrode and the counter electrode. The transparent electrode may be obtained by forming a thin film of fluorine-doped tin oxide (FTC) on the surface of a glass substrate (FTO glass), for example. Examples of metal oxide particles forming a porous layer on the surface of the transparent electrode include nano- and submicron particles of $TiO_2$, $ZnO$, $SnO_2$, $ZrO_2$, $Ta_2O_5$, $Nb_2O_5$, etc. The counter electrode may be an FTO glass having formed on the surface thereof a thin film of platinum, for example. The electrolyte may be an acetonitrile solution of iodine, lithium iodide, 4-t-butylpyridine, and 2,3-dimethyl-1-propylimidazolium iodide, for example. In the dye-sensitized solar cell thus configured, the sensitizing dye is excited by incident light passing through the transparent electrode, whereby electrons are injected into the surface of the metal oxide particles. The injected electrons are collected at the transparent electrode. Meanwhile, the sensitizing dye that has lost electrons receives electrons from the electrolyte, the electrolyte receives electrons from the counter electrode, and the counter electrode receives electrons from the transparent electrode through an external load. Through repeated cycles of such electron transfer, light energy is converted into electrical energy, performing a function as a cell, as widely known to those skilled in the art.

EXAMPLES

Hereinafter, the present invention will be described in detail with reference to examples, but the following descriptions are not to be construed as restrictive.

Example 1

Synthesis of Porphyrin Complex of the Present Invention No. 1 (Synthesis of cis-ZnP)

Synthesis was performed according to the following method.

[Chemical Formula 8]

Synthesis 1: cis-ZnP

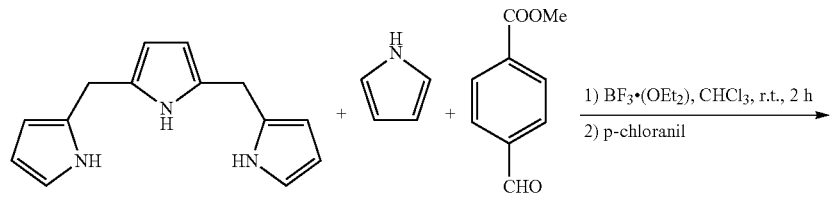

Taniguchi, S. et al. *Tetrahedron* 2001, 57. 2103.

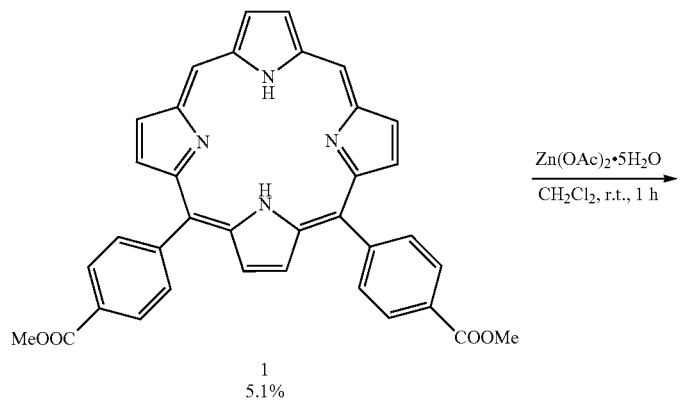

1
5.1%

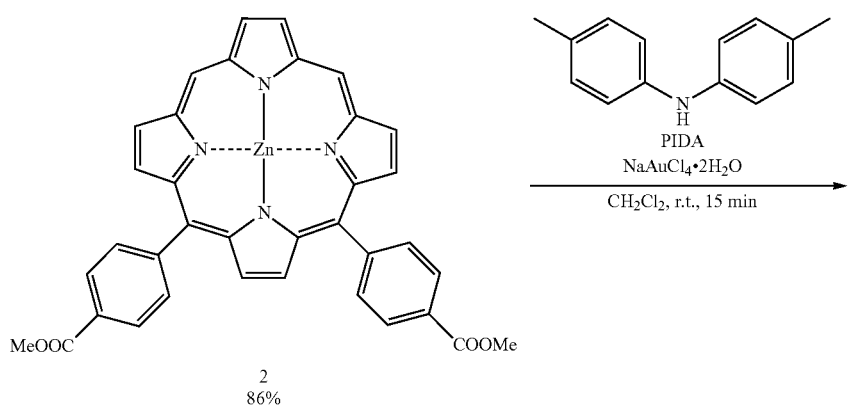

2
86%

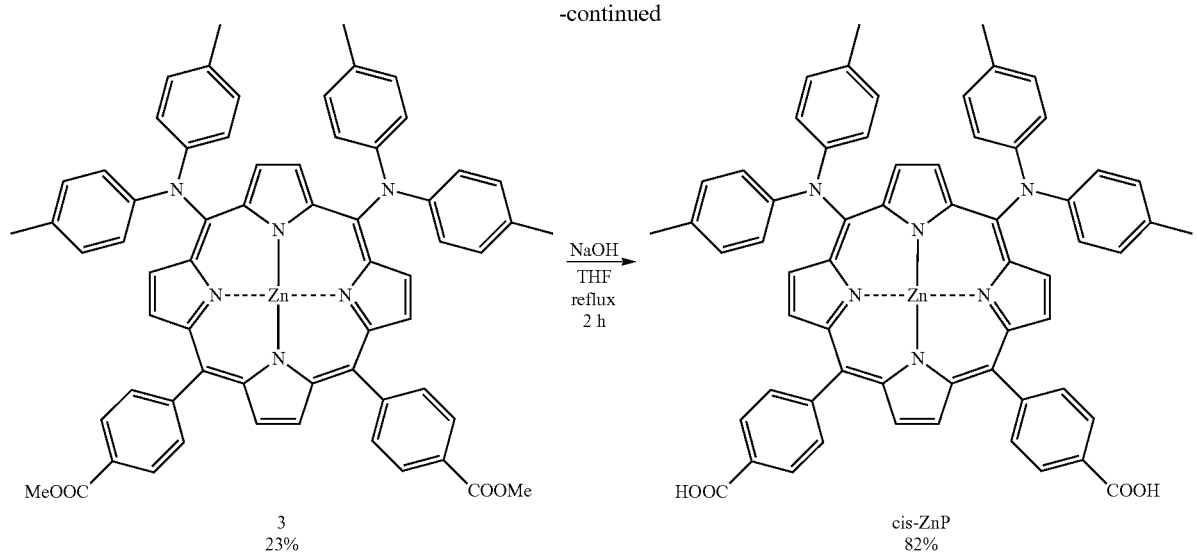

3
23%

PIDA = Phenyliodine diacetate = Iodobenzene diacetate
Shen, D.-M. et al. *J. Org. Chem.* 2009, 74, 206.

cis-ZnP
82%

(A) Synthesis of 5,10-bis(4-methoxycarboxyphenyl)porphyrin (1)

2 L of chloroform was added to a 2 L three-necked flask equipped with a nitrogen-introducing tube and a reflux tube, and nitrogen was bubbled at room temperature for 25 minutes. After purging with nitrogen, tripyrrane (1.444 g, 6.41 mmol), methyl 4-formylbenzoate (2.226 g, 13.6 mmol), pyrrole (4.4 g, 66 mmol), and a boron trifluoride-diethyl ether complex (0.4 mL) were added. The mixture was stirred in a nitrogen atmosphere at room temperature for 2 hours, and then p-chloranil (1.65 g, 6.72 mmol) was added and further stirred for 2 hours. Triethylamine (2 mL) was added to quench the reaction, then the reaction mixture was filtered through alumina, and the filtrate was concentrated under reduced pressure. The residue was purified on a silica gel column (dichloromethane). The resulting crude product was reprecipitated from dichloromethane/methanol to give a compound 1 as a purple solid (182.3 mg, 0.315 mmol) at a yield of 5.1%.

$^1$H NMR (400 Hz, CDCl$_3$): δ 10.32 (s, 2H, meso-H), 9.44 (s, 2H, β-pyrrolic), 9.35 (d, J=4.3 Hz, 2H, 3-pyrrolic), 8.96 (d, J=4.3 Hz, 2H, β-pyrrolic), 8.87 (s, 2H, β-pyrrolic), 8.45 (d, J=7.9 Hz, 2H, phenyl H), 8.30 (d, J=7.9 Hz, 2H, phenyl H), 4.12 (s, 6H, methyl H), −3.39 (br, 2H, inner H);

FAB-HRMS m/z calcd for C$_{36}$H$_{26}$N$_4$O$_4$: 578.1954. found: 578.1952;

FT-IR(KBr) ν$_{max}$ 3315, 2950, 1715, 1604, 1434, 1405, 1271, 1100, 956, 855, 736 cm$^{-1}$.

(B) Synthesis of 5,10-bis(4-methoxycarboxyphenyl)porphyrinatozinc(II) (2)

The compound 1 (182.3 mg, 0.315 mmol) and 30 mL of dichloromethane were added to a 100 mL recovery flask and stirred at room temperature. Subsequently, 1 mL of a saturated methanol solution of zinc acetate was added and stirred for 1 hour. The reaction mixture was filtered through silica gel (dichloromethane), and the filtrate was concentrated under reduced pressure. The resulting crude product was reprecipitated from dichloromethane/methanol to give a compound 2 as a purple solid (174.3 mg, 0.272 mmol) at a yield of 86%.

$^1$H NMR (400 Hz, CDCl$_3$): δ 10.23 (s, 2H, meso-H), 9.46 (s, 2H, β-pyrrolic), 9.41 (d, J=4.4 Hz, 2H, β-pyrrolic), 9.05 (d, J=4.4 Hz, 2H, β-pyrrolic), 8.97 (s, 2H, β-pyrrolic), 8.45 (d, J=7.9 Hz, 2H, phenyl H), 8.32 (d, J=7.9 Hz, 2H, phenyl H), 4.12 (s, 6H, methyl H);

FAB-HRMS m/z calcd for C$_{36}$H$_{24}$N$_4$O$_4$Zn: 640.1089. found: 640.1086;

FT-IR(KBr) ν$_{max}$ 3422, 3031, 2948, 1719, 1606, 1435, 1275, 1110, 993, 759 cm$^{-1}$.

(C) Synthesis of 5,10-bis(4-methoxycarboxyphenyl)-15,20-bis[N,N-bis(4-methylphenyl)amino]porphyrinatozinc(II) (3)

The compound 2 (174.3 mg, 0.272 mmol), iodobenzene diacetate (67.6 mg, 0.210 mmol), sodium tetrachloroaurate (III)dihydrate (166.8 mg, 0.419 mmol), di-p-tolylamine (267.8 mg, 1.357 mmol), and 10 mL of dichloromethane were added to a 100 mL recovery flask and stirred at room temperature for 15 minutes. Subsequently, 50 mL of a saturated aqueous solution of sodium thiosulfate was added to quench the reaction. The reaction mixture was transferred to a separating funnel, washed with distilled water, and dried over sodium sulfate. After the removal of the solvent, the residue was purified on a silica gel column (dichloromethane). The resulting crude product was dissolved in 20 mL of dichloromethane, and 1 mL of a saturated methanol solution of zinc acetate was added and stirred for 1 hour. The reaction mixture was filtered through silica gel (dichloromethane), and the filtrate was concentrated under reduced pressure. The resulting crude product was reprecipitated from dichloromethane/methanol to give a compound 3 as a green solid (65.6 mg, 0.0635 mmol) at a yield of 23%.

$^1$H NMR (400 Hz, CDCl$_3$): δ 9.27 (d, J=4.9 Hz, 2H, β-pyrrolic), 9.24 (s, 2H, β-pyrrolic), 8.73 (s, 2H, β-pyrrolic), 8.70 (d, J=4.9 Hz, 2H, β-pyrrolic), 8.37 (d, J=7.8 Hz, 4H, aryl H), 8.20 (d, J=7.8 Hz, 4H, aryl H), 7.17 (d, J=8.3 Hz, 8H, tolyl H), 6.97 (d, J=8.3 Hz, 8H, tolyl H), 4.09 (s, 6H, methyl H), 2.23 (s, 12H, methyl H);

FAB-HRMS m/z calcd for $C_{64}H_{50}N_6O_4Zn$: 1030.3185. found: 1030.3143;

FT-IR(KBr) $\nu_{max}$ 3428, 3025, 2949, 1724, 1700, 1606, 1505, 1271, 1100, 795 cm$^{-1}$.

(D) Synthesis of 5,10-bis(4-carboxyphenyl)-15,20-bis[N,N-bis(4-methylphenyl)amino]porphyrinatozinc (II) (cis-ZnP)

The compound 3 (10.3 mg, 0.0100 mmol) and 10 mL of tetrahydrofuran were added to a 100 mL recovery flask and dissolved. After that, 1 mL of a 5 M aqueous sodium hydroxide solution was added and refluxed for 12 hours. The reaction mixture was cooled to room temperature, and then 5 mL of 1 M hydrochloric acid and 20 mL of dichloromethane were added. The organic layer was washed with water, dried over sodium sulfate, and then filtered. The filtrate was concentrated by distillation under reduced pressure. The resulting crude product was reprecipitated from dichloromethane/hexane to give a compound cis-ZnP as a green solid (8.9 mg, 0.0089 mmol) at a yield of 89%.

$^1$H NMR (400 Hz, CDCl$_3$): δ 9.30 (d, J=4.4 Hz, 4H, β-pyrrolic), 9.25 (s, 2H, β-pyrrolic), 8.75 (d, J=4.4 Hz, 2H, β-pyrrolic), 8.73 (s, 2H, β-pyrrolic), 8.47 (d, J=7.8 Hz, 4H, aryl H), 8.27 (d, J=7.8 Hz, 4H, aryl H), 7.18 (d, J=8.8 Hz, 8H, tolyl H), 6.98 (d, J=8.8 Hz, 8H, tolyl H), 2.24 (s, 12H, methyl H);

FAB-HRMS m/z calcd for $C_{62}H_{46}N_6O_4Zn$: 1002.2872. found: 1002.2867;

FT-IR(KBr) $\nu_{max}$ 3420, 2923, 2848, 1723, 1700, 1607, 1507, 1339, 1272, 1112, 1000, 795, 667 cm$^{-1}$.

Example 2

Synthesis of Porphyrin Complex of the Present Invention No. 2 (Synthesis of trans-ZnP)

Synthesis was performed according to the following method.

[Chemical Formula 9]

Synthesis 2: trans-ZnP

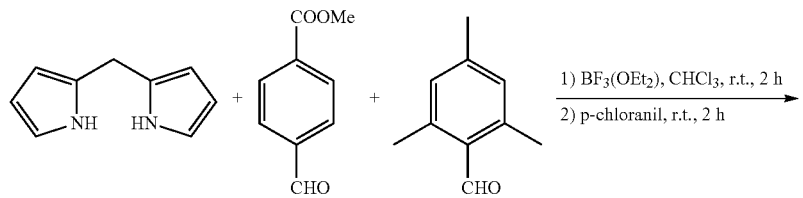

Cozzi, P. G. et al. *ChemSusChem* 2009, 2. 218

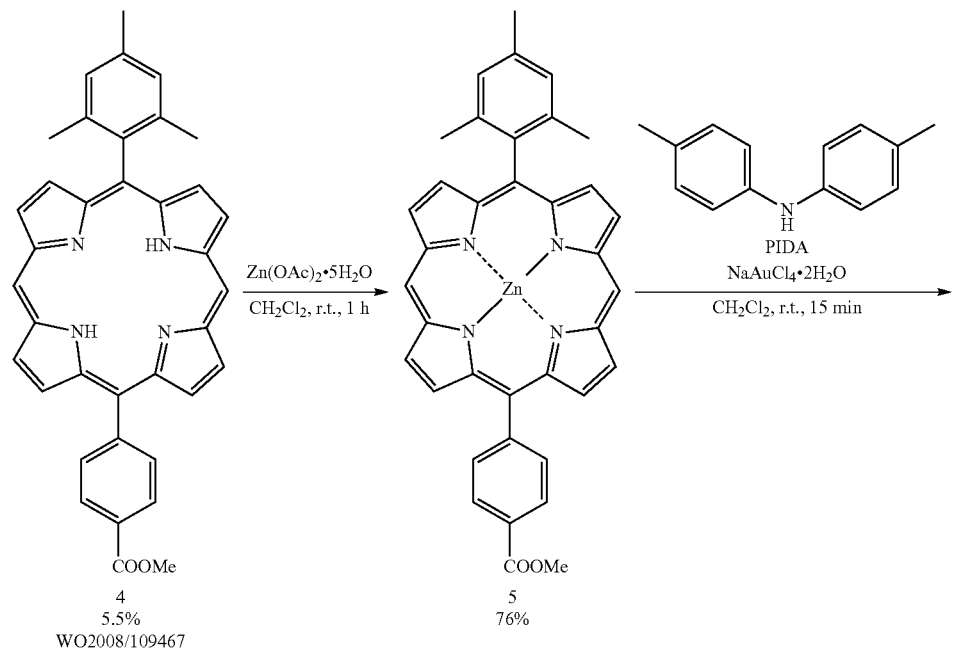

WO2008/109467

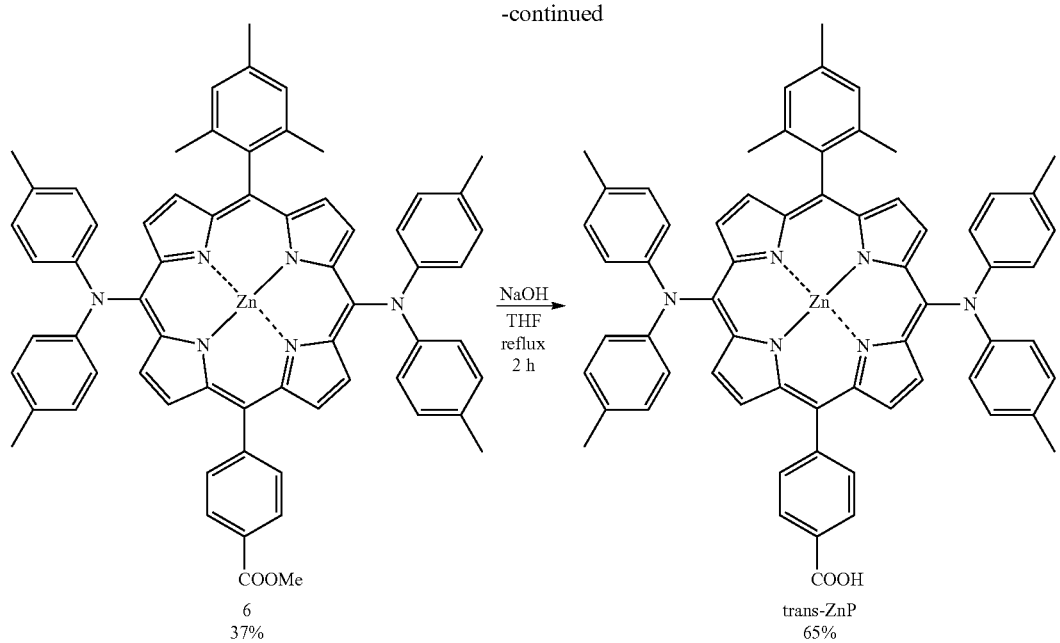

6
37%

→ NaOH / THF reflux 2 h → trans-ZnP
65%

PIDA = Phenyliodine diacetate = Iodobenzene diacetate
Shen, D. - M. et al. *J. Org. Chem.* 2009. 74, 206.

(A) Synthesis of 5-(4-methoxycarboxyphenyl)-15-(2,4,6-trimethylphenyl)porphyrin (4)

2 L of chloroform was added to a 2 L three-necked flask equipped with a nitrogen-introducing tube and a reflux tube, and nitrogen was bubbled at room temperature for 1 hour. After purging with nitrogen, dipyrromethane (3.569 g, 24.6 mmol), 2,4,6-trimethylbenzaldehyde (2.0 g, 13 mmol), methyl 4-formylbenzoate (2.024 g, 12.3 mmol), and a boron trifluoride-diethyl ether complex (0.4 mL) were added and stirred in a nitrogen atmosphere at room temperature for 2 hours. Further, p-chloranil (1.21 g, 4.92 mmol) was added and stirred for 2 hours. 2 mL of triethylamine was added to quench the reaction, then the reaction mixture was filtered through alumina, and the filtrate was concentrated under reduced pressure. The residue was purified on a silica gel column (dichloromethane/hexane=1:1). The resulting crude product was reprecipitated from dichloromethane/methanol to give a compound 4 as a purple solid (382.2 mg, 0.679 mmol) at a yield of 5.5%.

$^1$H NMR (400 Hz, CDCl$_3$): δ 10.28 (s, 2H, meso-H), 9.40 (d, J=4.4 Hz, 2H, β-pyrrolic), 9.34 (d, J=4.4 Hz, 2H, β-pyrrolic), 9.01 (d, J=4.4 Hz, 2H, β-pyrrolic), 8.90 (d, J 4.4 Hz, 2H, β-pyrrolic), 8.48 (d, J=7.8 Hz, 2H, phenyl H), 8.35 (d, J=7.8 Hz, 2H, phenyl H), 7.32 (s, 2H, phenyl H), 4.14 (s, 3H, methyl H), 2.66 (s, 3H, methyl H), 1.85 (s, 6H, methyl H), −3.10 (s, 2H, inner H);

FAB-HRMS m/z calcd for C$_{37}$H$_{30}$N$_4$O$_2$: 562.2369. found: 562.2362;

FT-IR(KBr) ν$_{max}$ 3280, 3099, 2952, 2916, 1726, 1607, 1436, 1277, 1113, 955, 856, 783, 753, 690 cm$^{-1}$.

(B) Synthesis of 5-(4-methoxycarboxyphenyl)-15-(2,4,6-trimethylphenyl)porphyrinatozinc(II) (5)

The compound 4 (382.2 mg, 0.679 mmol) and 50 mL of dichloromethane were added to a 200 mL recovery flask and stirred at room temperature. Subsequently, 5 mL of a saturated methanol solution of zinc acetate was added and stirred for 1 hour. The reaction mixture was filtered through silica gel (dichloromethane), and the filtrate was concentrated under reduced pressure. The resulting crude product was reprecipitated from dichloromethane/methanol to give a compound 5 as a purple solid (321.4 mg, 0.513 mmol) at a yield of 76%.

$^1$H NMR (400 Hz, CDCl$_3$): δ 10.31 (s, 2H, meso-H), 9.46 (d, J=4.4 Hz, 2H, β-pyrrolic), 9.41 (d, J=4.4 Hz, 2H, β-pyrrolic), 9.08 (d, J=4.4 Hz, 2H, β-pyrrolic), 8.99 (d, J=4.4 Hz, 2H, β-pyrrolic), 8.45 (d, J=7.9 Hz, 2H, phenyl H), 8.35 (d, J=7.9 Hz, 2H, phenyl H), 7.33 (s, 2H, phenyl H), 4.14 (s, 3H, methyl H), 2.67 (s, 3H, methyl H), 1.83 (s, 6H, methyl H);

FAB-HRMS m/z calcd for C$_{37}$H$_{28}$N$_4$O$_2$Zn: 624.1504. found: 624.1499;

FT-IR(KBr) ν$_{max}$ 3086, 2974, 2950, 2911, 1685, 1607, 1435, 1281, 1063, 996, 854, 789 cm$^{-1}$.

(C) Synthesis of 5-(4-methoxycarboxyphenyl)-10,20-bis[N,N-bis(4-methylphenyl)amino]-15-(2,4,6-trimethylphenyl)porphyrinatozinc(II) (6)

The compound 5 (321.4 mg, 0.513 mmol), iodobenzene diacetate (160.2 mg, 0.497 mmol), sodium tetrachloroaurate (III)dihydrate (287.3 mg, 0.722 mmol), di-p-tolylamine (498.5 mg, 2.53 mmol), and 20 mL of dichloromethane were added to a 100 mL recovery flask and stirred at room temperature for 15 minutes. 50 mL of a saturated aqueous solution of sodium thiosulfate was added to quench the reaction. The reaction mixture was then transferred to a separating funnel, washed with distilled water, and dried over sodium sulfate. After the removal of the solvent, the residue was purified on a silica gel column (dichloromethane:hexane=1:1). The resulting crude product was reprecipitated from dichloromethane/methanol to give a compound 6 as a green solid (193.3 mg, 0.190 mmol) at a yield of 37%.

$^1$H NMR (400 Hz, CDCl$_3$): δ 9.25 (d, J=4.9 Hz, 2H, β-pyrrolic), 9.20 (d, J=4.9 Hz, 2H, β-pyrrolic), 8.67 (d, J=4.9 Hz, 2H, β-pyrrolic), 8.59 (d, J=4.9 Hz, 2H, β-pyrrolic), 8.34 (d, J=7.8 Hz, 4H, aryl H), 8.19 (d, J=7.8 Hz, 4H, aryl H), 7.27 (s, 2H, phenyl H), 7.17 (d, J=8.3 Hz, 8H, tolyl H), 6.97 (d, J=8.3 Hz, 8H, tolyl H), 4.08 (s, 3H, methyl H), 2.58 (s, 3H, methyl H), 2.23 (s, 12H, methyl H), 1.81 (s, 6H, methyl H);

FAB-HRMS m/z calcd for $C_{65}H_{54}N_6O_2Zn$: 1014.3600. found: 1014.3578;

FT-IR(KBr) $\nu_{max}$ 3419, 2920, 2837, 1726, 1700, 1700, 1607, 1505, 1436, 1335, 1294, 999, 797 $cm^{-1}$.

(D) Synthesis of 5-(4-carboxyphenyl)-10,20-bis[N,N-bis(4-methylphenyl)amino]-15-(2,4,6-trimethylphenyl)porphyrinatozinc(II) (trans-ZnP)

The compound 6 (193.3 mg, 0.190 mmol) and 20 mL of tetrahydrofuran were added to a 100 mL recovery flask and dissolved. After that, 5 mL of a 5 M aqueous sodium hydroxide solution was added and refluxed for 6 hours. The reaction mixture was cooled to room temperature, and then 100 mL of 0.3 M hydrochloric acid and 100 mL of dichloromethane were added. The organic layer was washed with water and then dried over sodium sulfate. After the removal of the solvent by distillation under reduced pressure, the resulting crude product was reprecipitated from dichloromethane/hexane to give a compound trans-ZnP as a green solid (123.7 mg, 0.123 mmol) at a yield of 65%.

$^1$H NMR (400 Hz, CDCl$_3$): δ 9.26 (d, J=4.9 Hz, 2H, β-pyrrolic), 9.20 (d, J=4.9 Hz, 2H, β-pyrrolic), 8.69 (d, J=4.9 Hz, 2H, β-pyrrolic), 8.60 (d, J=4.9 Hz, 2H, β-pyrrolic), 8.41 (d, J=8.4 Hz, 4H, aryl H), 8.22 (d, J=8.4 Hz, 4H, aryl H), 7.27 (s, 2H, phenyl H), 7.17 (d, J=8.3 Hz, 8H, tolyl H), 6.97 (d, J=8.3 Hz, 8H, tolyl H), 2.58 (s, 3H, methyl H), 2.23 (s, 12H, methyl H), 1.81 (s, 6H, methyl H);

FAB-HRMS m/z calcd for $C_{64}H_{52}N_6O_2Zn$: 1000.3443. found: 1000.3431;

FT-IR(KBr) $\nu_{max}$ 3022, 2914, 2858, 1739, 1684, 1607, 1507, 1334, 1294, 998, 798 $cm^{-1}$.

Example 3

Synthesis of Porphyrin Complex of the Present Invention No. 3 (Synthesis of mono-ZnP)

Synthesis was performed according to the following method.

[Chemical Formula 10]

Synthesis 3: mono-ZnP

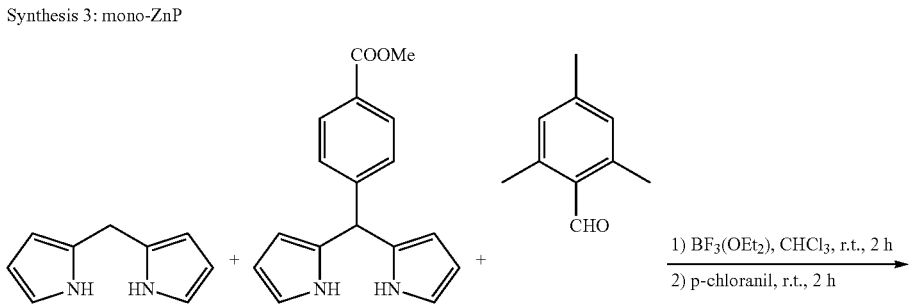

Lee, C.-H. et al., *Tetrahedron. Lett.* 2000, 41. 4609

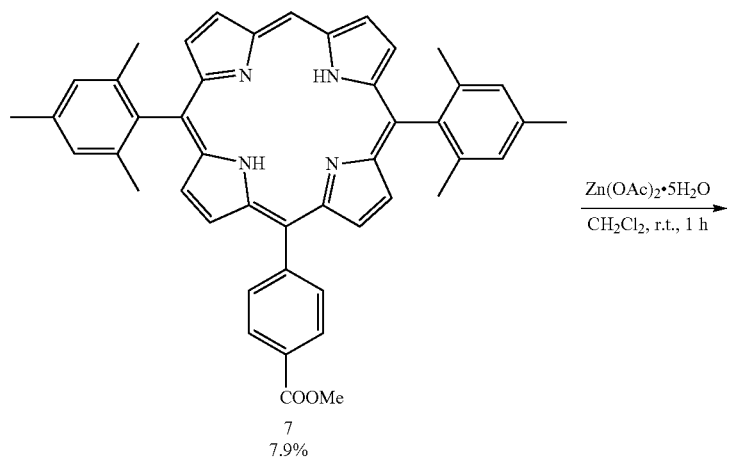

7
7.9%

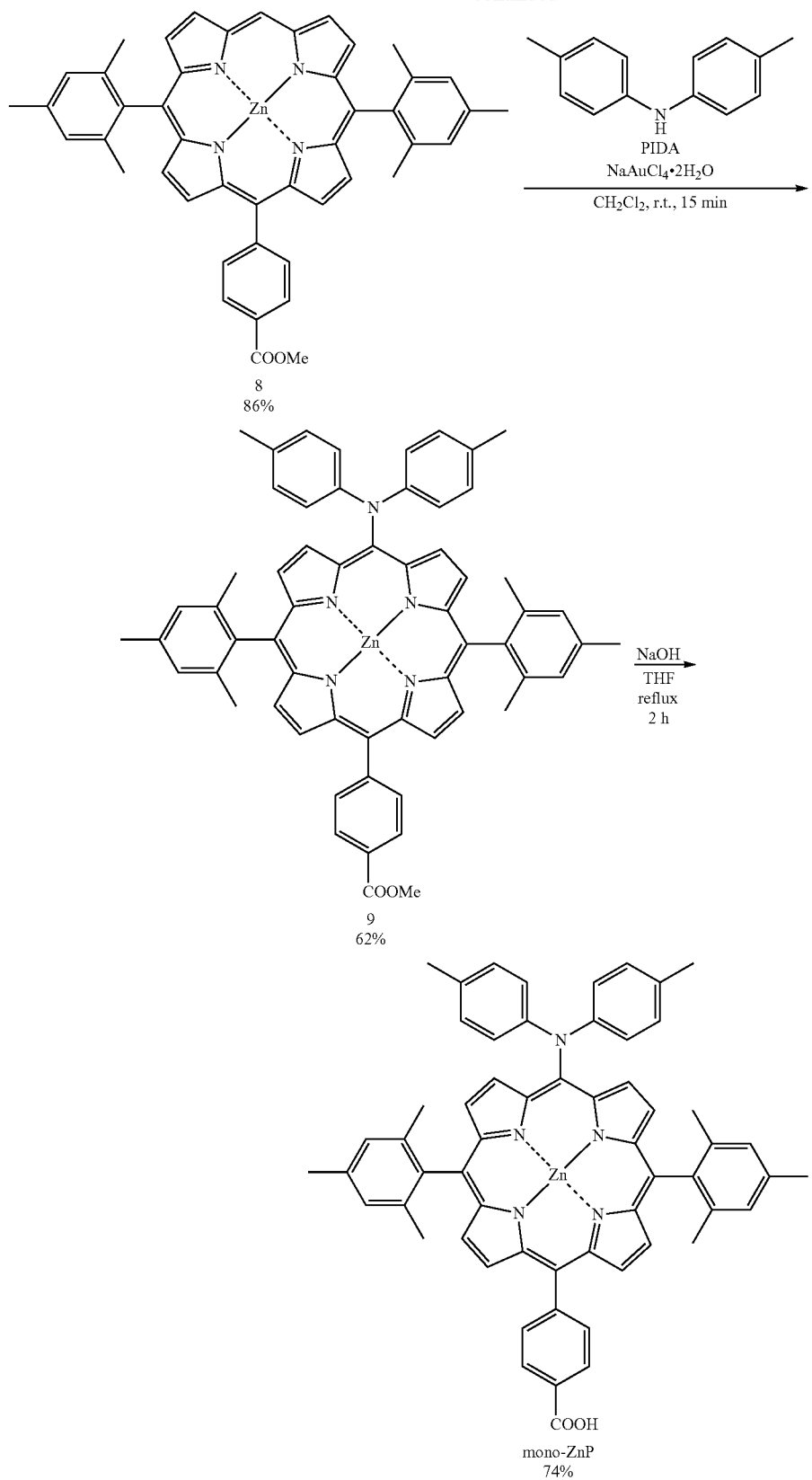
PIDA = Phenyliodine diacetate = Iodobenzene diacetate
Shen, D. - M. et al. *J. Org. Chem.* 2009. 74, 206.

(A) Synthesis of 5-(4-methoxycarboxyphenyl)-10, 20-bis(2,4,6-trimethylphenyl)porphyrin (7)

1.4 L of chloroform was added to a 2 L three-necked flask equipped with a nitrogen-introducing tube and a reflux tube, and nitrogen was bubbled at room temperature for 1 hour. Subsequently, dipyrromethane (227.1 mg, 1.90 mmol), 4-methoxycarboxyphenyl dipyrromethane (507.4 mg, 1.81 mmol), 2,4,6-trimethylbenzaldehyde (0.58 g, 3.9 mmol), and a boron trifluoride-diethyl ether complex (0.2 ml) were added and stirred in a nitrogen atmosphere at room temperature for 2 hours. Further, p-chloranil (0.61 g, 2.5=01) was added and stirred for 2 hours. 1 mL of triethylamine was added to quench the reaction, then the reaction mixture was filtered through alumina, and the filtrate was concentrated under reduced pressure. The residue was purified on a silica gel column (dichloromethane/hexane=1:1). The resulting crude product was reprecipitated from dichloromethane/methanol to give a compound 7 as a purple solid (97.8 mg, 0.144 mmol) at a yield of 7.9%.

$^1$H NMR (400 Hz, CDCl$_3$): δ 10.14 (s, 2H, meso-H), 9.28 (d, J=4.9 Hz, 2H, β-pyrrolic), 8.83 (d, J=4.9 Hz, 2H, β-pyrrolic), 8.76 (d, J=4.9 Hz, 2H, β-pyrrolic), 8.74 (d, J 4.9 Hz, 2H, β-pyrrolic), 8.42 (d, J=8.3 Hz, 2H, phenyl H), 8.31 (d, J=8.3 Hz, 2H, phenyl H), 7.30 (s, 4H, phenyl H), 4.10 (s, 3H, methyl H), 2.64 (s, 6H, methyl H), 1.84 (s, 12H, methyl H), −2.91 (s, 2H, inner H);

FAB-HRMS m/z calcd for C$_{46}$H$_{40}$N$_4$O$_2$: 680.3151. found: 680.3156;

FT-IR(KBr) $v_{max}$ 3314, 2917, 1724, 1275, 1101, 966, 798, 677 cm$^{-1}$.

(B) Synthesis of 5-(4-methoxycarboxyphenyl)-10, 20-bis(2,4,6-trimethylphenyl)porphyrinatozinc(II) (8)

The compound 7 (97.8 mg, 0.144 mmol) and 50 mL of dichloromethane were added to a 100 mL recovery flask and stirred at room temperature. Subsequently, 3 mL of a saturated methanol solution of zinc acetate was added and stirred for 1 hour. The reaction mixture was filtered through silica gel (dichloromethane), and the filtrate was concentrated under reduced pressure. The residue was purified on a silica gel column (dichloromethane/hexane=2:1). The resulting crude product was reprecipitated from dichloromethane/methanol to give a compound 8 as a purple solid (87.5 mg, 0.118 mmol) at a yield of 82%.

$^1$H NMR (400 Hz, CDCl$_3$): δ 10.19 (s, 2H, meso-H), 9.35 (d, J=4.4 Hz, 2H, β-pyrrolic), 8.92 (d, J=4.4 Hz, 2H, β-pyrrolic), 8.85 (d, J=4.4 Hz, 2H, β-pyrrolic), 8.82 (d, J=4.4 Hz, 2H, β-pyrrolic), 8.41 (d, J=8.3 Hz, 2H, phenyl H), 8.32 (d, J=8.3 Hz, 2H, phenyl H), 7.30 (s, 4H, phenyl H), 4.10 (s, 3H, methyl H), 2.65 (s, 6H, methyl H), 1.82 (s, 12H, methyl H);

FAB-HRMS m/z calcd for C$_{46}$H$_{38}$N$_4$O$_2$Zn: 742.2295. found: 742.2285;

FT-IR(KBr) $v_{max}$ 3430, 2947, 2915, 1725, 1700, 1607, 1437, 1274, 996, 795, 722 cm$^{-1}$.

(C) Synthesis of 5-(4-methoxycarboxyphenyl)-10, 20-bis(2,4,6-trimethylphenyl)-15-[N,N-bis(4-methylphenyl)amino]porphyrinatozinc(II) (9)

The compound 8 (87.5 mg, 0.118 mmol), iodobenzene diacetate (41.5 mg, 0.129 mmol), sodium tetrachloroaurate (III)dihydrate (77.0 mg, 0.194 mmol), di-p-tolylamine (69.8 mg, 0.354 mmol), and 5 mL of dichloromethane were added to a 100 mL recovery flask and stirred at room temperature for 10 minutes. 50 mL of a saturated aqueous solution of sodium thiosulfate was added to quench the reaction. The reaction mixture was then transferred to a separating funnel, washed with distilled water, and dried over sodium sulfate, and the solvent was distilled off. The resulting residue was dissolved in 20 mL of dichloromethane, and 1 mL of a saturated methanol solution of zinc acetate was added and stirred for 1 hour. The reaction mixture was filtered through silica gel (dichloromethane), and the filtrate was concentrated under reduced pressure. The residue was purified on a silica gel column (dichloromethane:hexane=2:1). The resulting crude product was reprecipitated from dichloromethane/methanol to give a compound 9 as a green solid (68.9 mg, 0.0733 mmol) at a yield of 62%.

$^1$H NMR (400 Hz, CDCl$_3$): δ 9.26 (d, J=4.9 Hz, 2H, β-pyrrolic), 8.74 (d, J=4.9 Hz, 2H, β-pyrrolic), 8.71 (d, J=4.9 Hz, 2H, β-pyrrolic), 8.65 (d, J=4.9 Hz, 2H, β-pyrrolic), 8.40 (d, J=7.8 Hz, 4H, aryl H), 8.29 (d, J=7.8 Hz, 4H, aryl H), 7.26 (s, 4H, phenyl H), 7.20 (d, J=8.3 Hz, 4H, tolyl H), 6.97 (d, J=8.3 Hz, 4H, tolyl H), 4.10 (s, 3H, methyl H), 2.60 (s, 6H, methyl H), 2.24 (s, 6H, methyl H), 1.81 (s, 12H, methyl H);

FAB-HRMS m/z calcd for C$_{60}$H$_{51}$N$_5$O$_2$Zn: 937.3334. found: 937.3320;

FT-IR(KBr) $v_{max}$ 2948, 2919, 1726, 1700, 1607, 1506, 1269, 999, 798, 719 cm$^{-1}$.

(D) Synthesis of 5-(4-carboxyphenyl)-10,20-bis(2,4, 6-trimethylphenyl)-15-[N,N-bis(4-methylphenyl)amino]porphyrinatozinc(II) (mono-ZnP)

The compound 9 (68.9 mg, 0.0733 mmol) and 30 mL of tetrahydrofuran were added to a 100 mL recovery flask and dissolved. After that, 1 mL of a 5M aqueous sodium hydroxide solution was added and refluxed for 12 hours. The reaction mixture was cooled to room temperature, and then 5 mL of 1 M hydrochloric acid and 30 mL of dichloromethane were added. The organic layer was washed with water, dried over sodium sulfate, and then filtered, followed by the removal of the solvent by distillation under reduced pressure. The resulting crude product was reprecipitated from methanol+acetone/water to give a compound mono-ZnP as a green solid (50.2 mg, 0.0544=01) at a yield of 74%.

$^1$H NMR (400 Hz, CDCl$_3$): δ 9.27 (d, J=4.9 Hz, 2H, β-pyrrolic), 8.76 (d, J=4.9 Hz, 2H, β-pyrrolic), 8.73 (d, J=4.9 Hz, 2H, β-pyrrolic), 8.65 (d, J=4.9 Hz, 2H, β-pyrrolic), 8.48 (d, J=7.8 Hz, 4H, aryl H), 8.33 (d, J=7.8 Hz, 4H, aryl H), 7.26 (s, 4H, phenyl H), 7.21 (d, J=8.3 Hz, 4H, tolyl H), 6.98 (d, J=8.3 Hz, 4H, tolyl H), 2.61 (s, 6H, methyl H), 2.24 (s, 6H, methyl H), 1.82 (s, 12H, methyl H);

FAB-HRMS m/z calcd for C$_{59}$H$_{49}$N$_5$O$_2$Zn: 923.3178. found: 923.3145;

FT-IR(KBr) $v_{max}$ 3422, 2919, 2855, 1734, 1695, 1606, 1505, 1336, 1265, 999, 810, 719 cm$^{-1}$.

Example 4

Synthesis of Porphyrin Complex of the Present Invention No. 4 (Synthesis of bis-ZnP)

Synthesis was performed according to the following method.

Synthesis 4: bis-ZnP
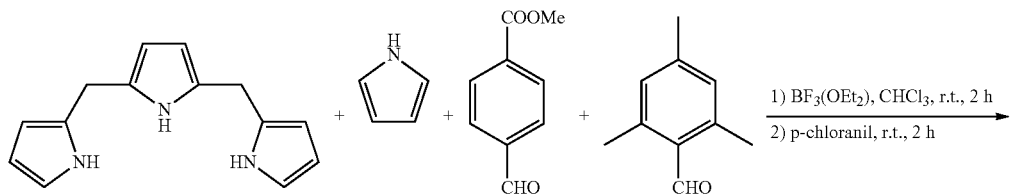
Taniguchi, S. et al. *Tetrahedron* 2001, 57. 2103
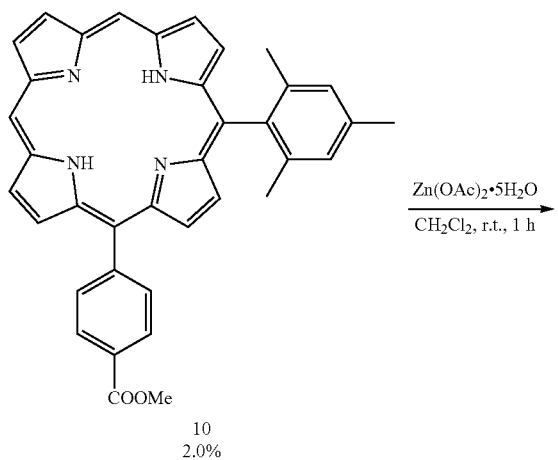
10
2.0%
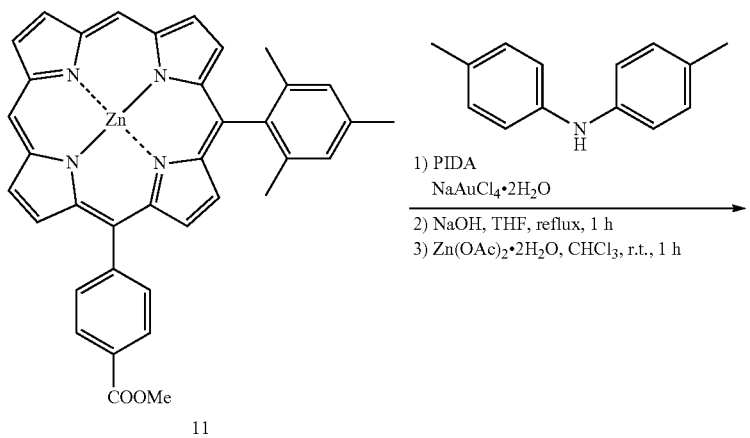
11
84.5%

-continued

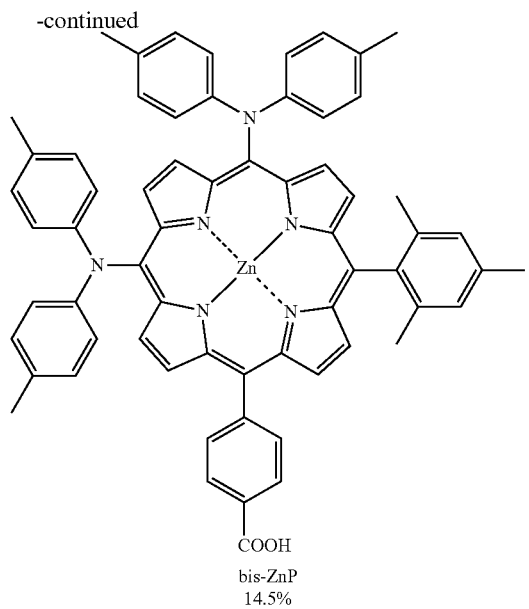

bis-ZnP
14.5%

PIDA = Phenylionine diacetate = Iodobenzene diacetate
Shen, D. - M. et al. *J. Org. Chem.* 2009. 74, 206.

(A) Synthesis of 5-(4-methoxycarboxyphenyl)-10-(2,4,6-trimethylphenyl)porphyrin (10)

2 L of chloroform was added to a 2 L three-necked flask equipped with a nitrogen-introducing tube and a reflux tube, and nitrogen was bubbled at room temperature for 20 minutes. After the flask was purged with nitrogen and protected from light, tripyrrane (2.14 g, 9.50 mmol), methyl 4-formylbenzoate (1.746 g, 10.64 mmol), 2,4,6-trimethylbenzaldehyde (1.576 g, 10.63 mmol), pyrrole (0.75 g, 11.18 mmol), and a boron trifluoride-diethyl ether complex (0.5 mL) were added and stirred for 1 hour and 30 minutes. Further, p-chloranil (3.32 g, 13.5 mmol) was added and stirred for 1 hour and 30 minutes. The reaction mixture was filtrated through alumina, and the filtrate was concentrated under reduced pressure. The residue was purified on a silica gel column (dichloromethane/hexane=1:1 to 4:1 gradient) to give a compound 10 as a purple solid (108.8 mg, 0.193 mmol) at a yield of 2.0%.

$^1$H NMR (400 Hz, CDCl$_3$): δ 10.25 (s, 1H, meso-H), 10.22 (s, 1H, meso-H), 9.46 (s, 2H, β-pyrrolic), 9.37 (d, J=4.4 Hz, 1H, β-pyrrolic), 9.31 (d, J=4.4 Hz, 1H, β-pyrrolic), 8.97 (d, J=4.4 Hz, 1H, β-pyrrolic), 8.88 (d, J=4.4 Hz, 1H, β-pyrrolic), 8.82 (d, J=4.9 Hz, 1H, β-pyrrolic), 8.80 (d, J=4.9 Hz, 1H, β-pyrrolic), 8.45 (d, J=8.3 Hz, 2H, phenyl), 8.33 (d, J=8.3 Hz, 2H, phenyl), 7.30 (s, 2H, phenyl), 4.12 (s, 3H, methyl), 2.65 (s, 3H, methyl), 1.82 (s, 6H, methyl), −3.28 (s, 2H, innerH);

HRMS m/z calcd for C$_{37}$H$_{31}$N$_4$O$_2$[M+H]$^+$: 563.2442. found 563.2417;

FT-IR(KBr) ν$_{max}$ 3400, 2964, 2555, 1803, 1720, 1674, 1607, 1436, 1292, 1108, 1066, 997, 848, 793 cm$^{-1}$.

(B) Synthesis of 5-(4-methoxycarboxyphenyl)-10-(2,4,6-trimethylphenyl)porphyrinatozinc(II) (11)

The compound 10 (100.1 mg, 0.178 mmol) and 20 mL of chloroform were added to a 100 mL recovery flask. Further, zinc acetate dihydrate (254 mg, 1.16 mmol) was dissolved in 2 mL of methanol, added to the flask, and stirred at room temperature for 2 hours. The reaction mixture was filtered through silica gel (chloroform), and the filtrate was concentrated under reduced pressure. The residue was purified on a silica gel column (dichloromethane/hexane=3:2 to 2:1 gradient) to give a compound 11 as a purple solid (94.2 mg, 0.151 mmol) at a yield of 84.5%.

$^1$H NMR (400 Hz, CDCl$_3$): δ 9.97 (s, 1H, meso-H), 9.75 (s, 1H, meso-H), 9.33 (d, J=4.9 Hz, 1H, β-pyrrolic), 9.14 (d, J=4.4 Hz, 1H, β-pyrrolic), 9.06 (d, J=4.4 Hz, 1H, β-pyrrolic), 8.98 (d, J=3.9 Hz, 1H, β-pyrrolic), 8.97 (d, J=3.9 Hz, 1H, β-pyrrolic), 8.90 (m, 3H, β-pyrrolic), 8.31 (d, J=8.3 Hz, 2H, phenyl), 8.28 (d, J=8.3 Hz, 2H, phenyl), 7.31 (s, 2H, phenyl), 3.97 (s, 3H, methyl), 2.65 (s, 3H, methyl), 1.86 (s, 6H, methyl);

HRMS m/z calcd for C$_{37}$H$_{28}$N$_4$O$_2$Zn: 624.1498. found 634.1474;

FT-IR(KBr) ν$_{max}$ 3309, 2951, 1717, 1604, 1407, 1281, 1111, 948, 851, 798 cm$^{-1}$.

(C) Synthesis of 5-(4-carboxyphenyl)-10-(2,4,6-trimethylphenyl)-15,20-[N,N-bis(4-methylphenyl)amino]porphyrinatozinc(II) (bis-ZnP)

The compound 11 (82.2 mg, 0.131 mmol), iodobenzene diacetate (45.0 mg, 0.134 mmol), sodium tetrachloroaurate (III)dihydrate (95.0 mg, 0.239 mmol), di-p-tolylamine (127.9 mg, 0.648 mmol), and 10 mL of dichloromethane were added to a 50 mL recovery flask and stirred at room temperature for 15 minutes. 20 mL of a saturated aqueous solution of sodium thiosulfate was added to quench the reaction. The mixture was then partitioned three times with distilled water, followed by dehydration over sodium sulfate, concentration under reduced pressure, and vacuum drying. Next, the mixture was placed in a 50 mL recovery flask and dissolved in 10 mL of tetrahydrofuran, and then 5 mL of a 2 M aqueous sodium hydroxide solution was added and refluxed for 1 hour. After the reaction mixture was cooled to room temperature, 10 mL of 1 M hydrochloric acid and 30 mL of dichloromethane were added. The mixture was then sequentially partitioned with a saturated aqueous solution of sodium hydrogen carbonate and distilled water (twice), further followed by dehydration over sodium sulfate, concentration under reduced pressure, and vacuum drying. Subsequently, the mixture and 20 mL of chloroform were added to a 50 mL recovery flask. Further, zinc acetate dihydrate (212 mg, 0.97 mmol) was dissolved in 2 mL of methanol, added to the flask, and stirred at room temperature for 1 hour. The reaction mixture was purified on a silica gel column (dichloromethane/ethyl acetate=2:1) to give a compound bis-ZnP as a green solid (19.0 mg, 0.019 mmol) at a yield of 14.5%.

$^1$H NMR (400 Hz, CDCl$_3$): δ 9.26 (d, J=4.4 Hz, 1H, β-pyrrolic), 9.22 (s, 2H, β-pyrrolic), 9.20 (d, J=4.4 Hz, 1H, β-pyrrolic), 8.70 (d, J=4.4 Hz, 1H, β-pyrrolic), 8.69 (d, J=4.4 Hz, 1H, β-pyrrolic), 8.66 (d, J=4.4 Hz, 1H, β-pyrrolic), 8.43 (d, J=7.8 Hz, 2H, phenyl), 8.26 (d, J=7.8 Hz, 2H, phenyl), 7.23 (s, 2H, phenyl), 7.18 (d, J=5.4 Hz, 4H, tolyl), 7.16 (d, J=5.4 Hz, 4H, tolyl), 6.98 (d, J=3.4 Hz, 4H, tolyl), 6.96 (d, J=3.4 Hz, 4H, tolyl), 2.60 (s, 3H, methyl), 2.23 (s, 12H, methyl), 1.81 (s, 6H, methyl);

HRMS m/z calcd for $C_{64}H_{52}N_6O_2Zn$: 1000.3438. found 1000.3406;

FT-IR(KBr) $v_{max}$ 3400, 2923, 2854, 1700, 1609, 1507, 1337, 1295, 1267, 1065, 998, 796 cm$^{-1}$.

Example 5

Figure 2:
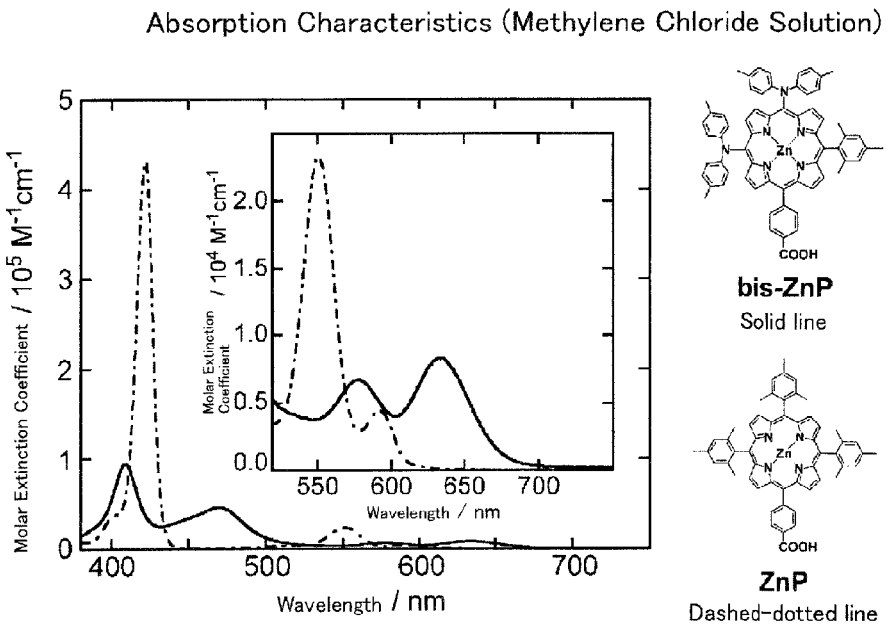
FIG. 2: A spectrum showing the results of the evaluation of the light absorption characteristics of a porphyrin complex of the present invention (bis-ZnP) in the Examples.

Evaluation of Light Absorption Characteristics of Porphyrin Complex of the Present Invention FIG. 1 shows evaluation results from methylene chloride solutions of cis-ZnP, trans-ZnP, and mono-ZnP, respectively. FIG. 2 shows evaluation results from a methylene chloride solution of bis-ZnP. Incidentally, FIG. 1 and FIG. 2 also show evaluation results from a methylene chloride solution of ZnP as a comparative example. As is clear from FIG. 1 and FIG. 2, it was found that when a diarylamino group is introduced into a meso position of a porphyrin ring, light absorption broadens and shifts to a longer wavelength, whereby light collection characteristics are improved, and also that the effectiveness is higher when the number of diarylamino groups introduced is 2 than when it is 1.

Example 6

Energy Diagram of Porphyrin Complex of the Present Invention

Figure 3:
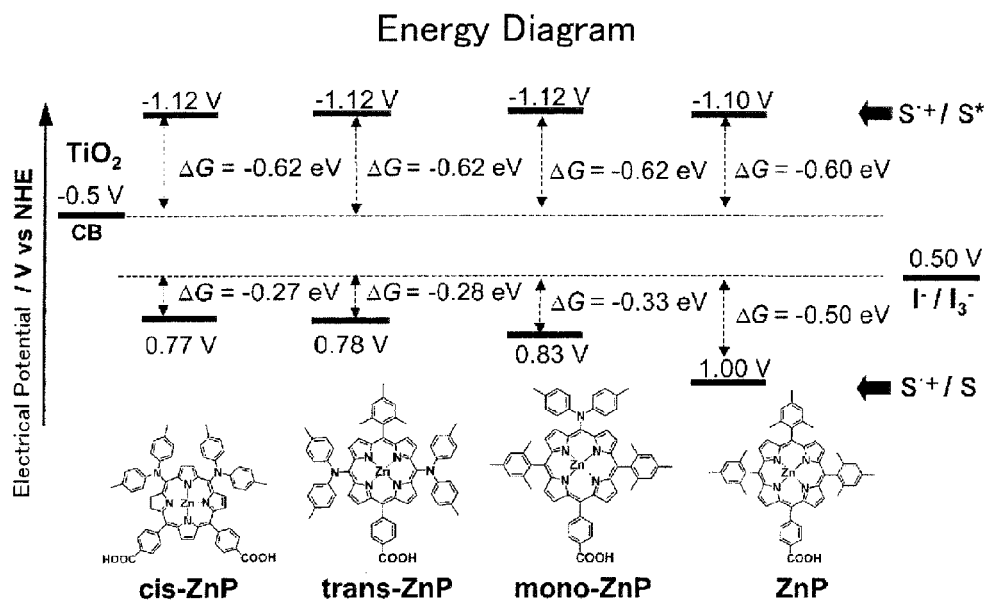
FIG. 3: Energy diagrams of porphyrin complexes of the present invention (cis-ZnP, trans-ZnP, and mono-ZnP) in the Examples.
Figure 4:
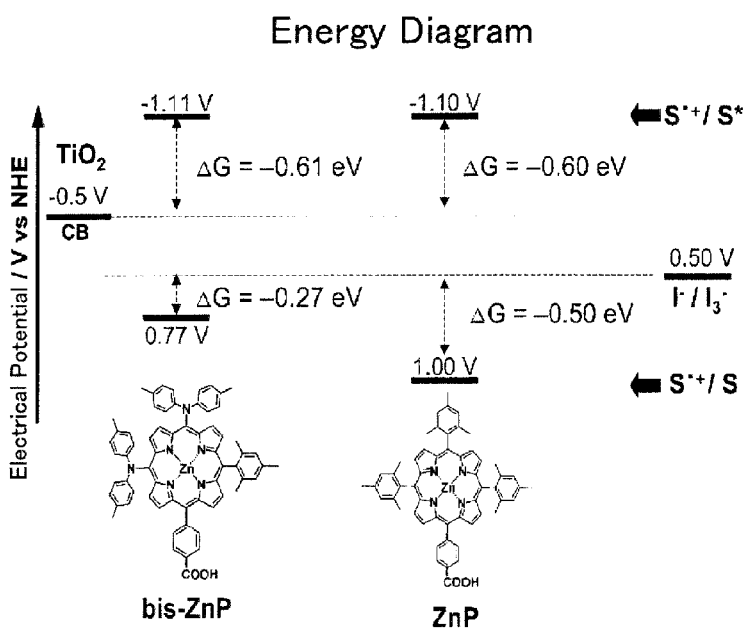
FIG. 4: An energy diagram of a porphyrin complex of the present invention (bis-ZnP) in the Examples.

FIG. 3 shows energy diagrams of cis-ZnP, trans-ZnP, and mono-ZnP, respectively. FIG. 4 shows an energy diagram of bis-ZnP. Incidentally, FIG. 3 and FIG. 4 also show an energy diagram of ZnP as a comparative example. As is clear from FIG. 3 and FIG. 4, it was found that when a diarylamino group is introduced into a meso position of a porphyrin ring, only the HOMO level increases, and the HOMO-LUMO gap decreases, but an electrical potential difference sufficient for electron donation from iodine is maintained, and also that the degree of the increase in the HOMO level is higher when the number of diarylamino groups introduced is 2 than when it is 1.

Example 7

Production of Dye-Sensitized Solar Cell Using Porphyrin Complex of the Present Invention as Sensitizing Dye and Evaluation Thereof A titanium oxide electrode including a porous layer of TiO$_2$ particles formed on the surface of a transparent electrode was produced in accordance with the method described in Graetzel, M. et al., Chem. Commun., 2005, 4351. As the transparent electrode, an FTO glass was used. The porous layer formed on the surface thereof had a laminate structure including a layer of TiO$_2$ particles having an average particle size of 20 nm, about 12 μm thick, and a layer of TiO$_2$ particles having an average particle size of 400 nm, about 4 μm thick. The produced titanium oxide electrode was immersed in a 0.2 mM methanol solution of a porphyrin complex of the present invention to allow the porphyrin complex of the present invention to be adsorbed to the surface of each TiO$_2$ particle, thereby giving a dye-modified titanium oxide electrode. A dye-sensitized solar cell was produced using the dye-modified titanium oxide electrode together with, as a counter electrode, an FTO glass having a thin film of platinum formed on the surface thereof and, as an electrolyte, an acetonitrile solution of 0.05 M iodine, 0.1 M lithium iodide, 0.5 M 4-t-butylpyridine, and 0.6 M 2,3-dimethyl-1-propylimidazolium iodide.

Figure 5:
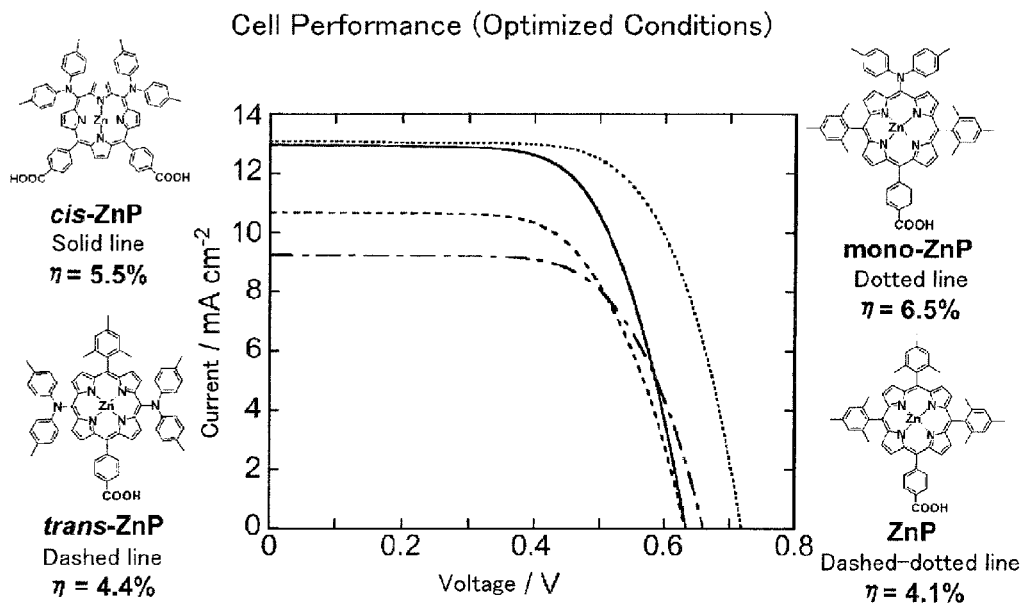
FIG. 5: Current-voltage curves showing the results of the evaluation of the cell performance of dye-sensitized solar cells produced using porphyrin complexes of the present invention (cis-ZnP, trans-ZnP, and mono-ZnP) in the Examples.
Figure 6:
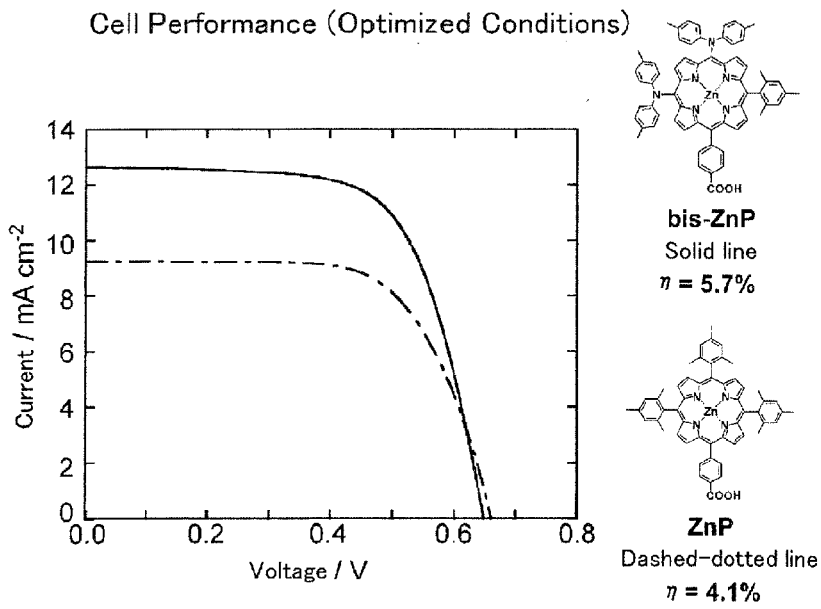
FIG. 6: A current-voltage curve showing the results of the evaluation of the cell performance of a dye-sensitized solar cell produced using a porphyrin complex of the present invention (bis-ZnP) in the Examples.
Figure 7:
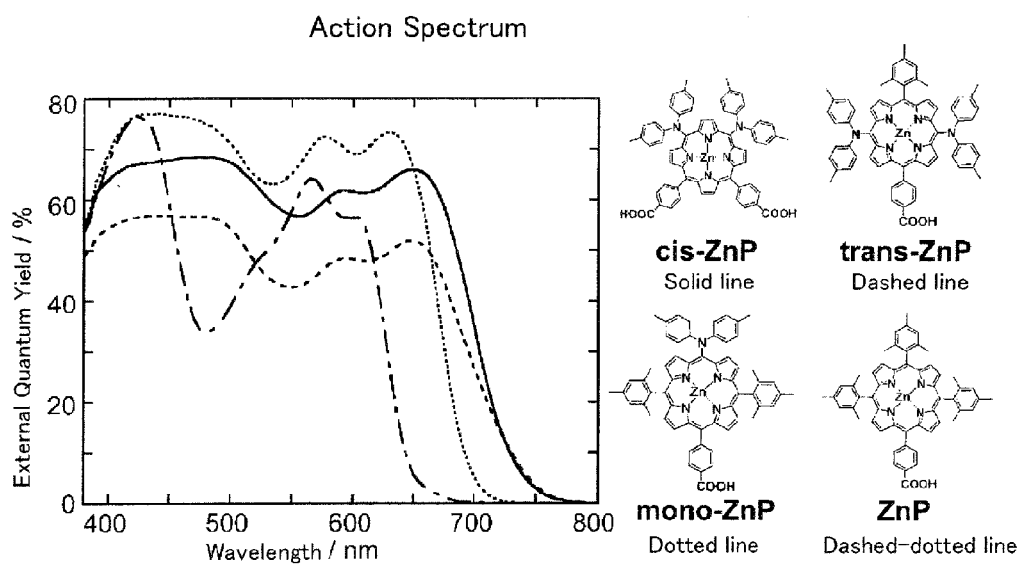
FIG. 7: Action spectra showing the results of the evaluation of the cell performance of dye-sensitized solar cells produced using porphyrin complexes of the present invention (cis-ZnP, trans-ZnP, and mono-ZnP) in the Examples.
Figure 8:
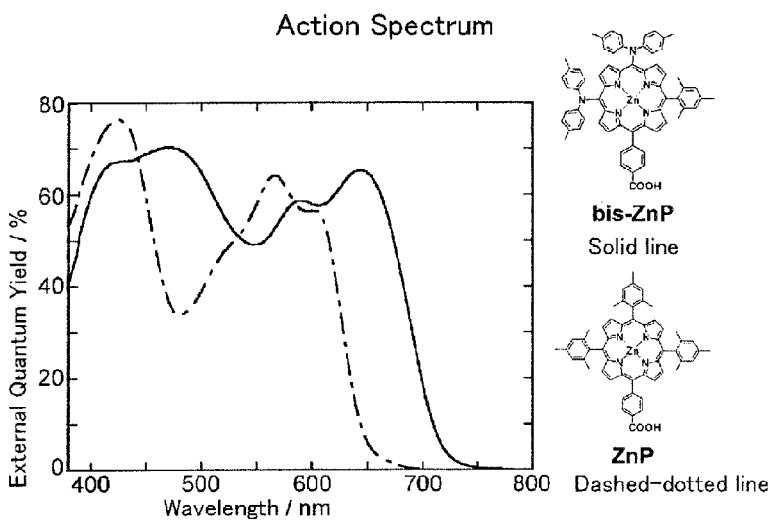
FIG. 8: An action spectrum showing the results of the evaluation of the cell performance of a dye-sensitized solar cell produced using a porphyrin complex of the present invention (bis-ZnP) in the Examples.
Figure 9:
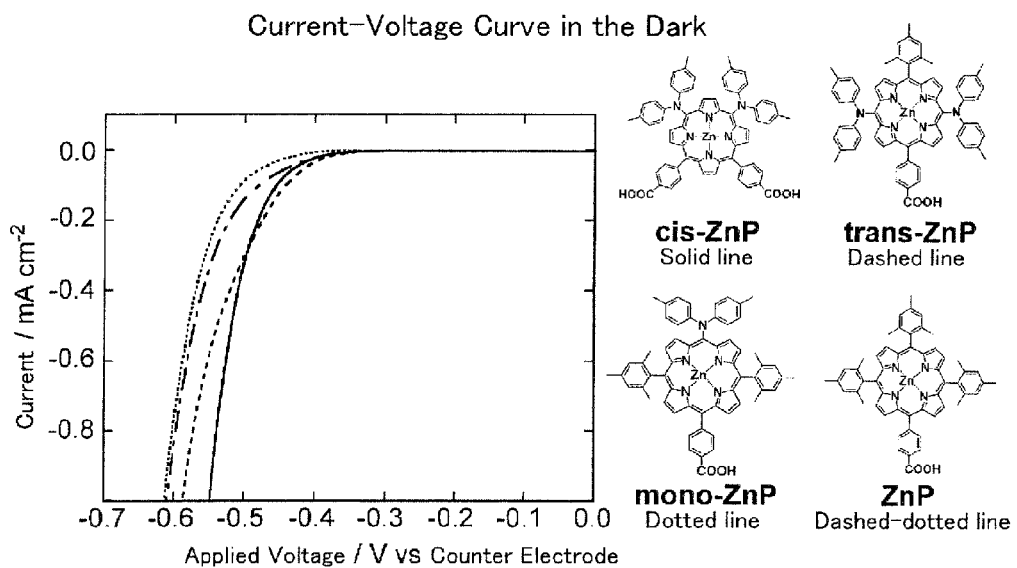
FIG. 9: Current-voltage curves in the dark showing the results of the evaluation of the cell performance of dye-sensitized solar cells produced using porphyrin complexes of the present invention (cis-ZnP, trans-ZnP, and mono-ZnP) in the Examples.
Figure 10:
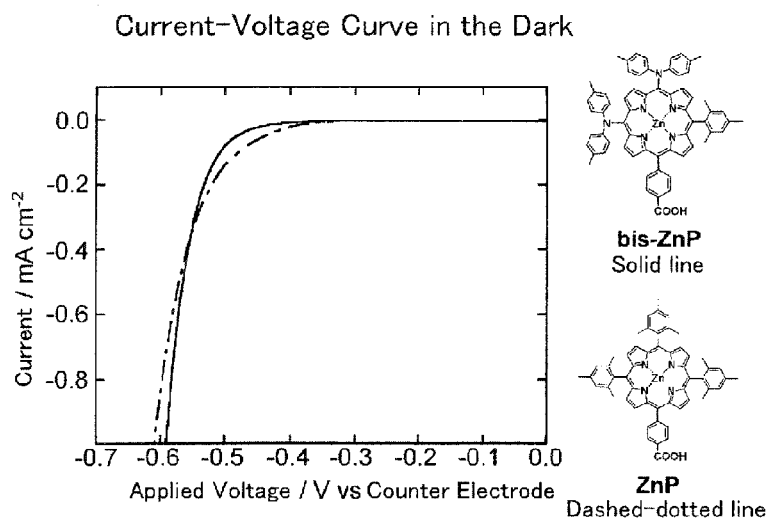
FIG. 10: A current-voltage curve in the dark showing the results of the evaluation of the cell performance of a dye-sensitized solar cell produced using a porphyrin complex of the present invention (bis-ZnP) in the Examples.

The results of the evaluation of the cell performance of dye-sensitized solar cells produced using cis-ZnP, trans-ZnP, and mono-ZnP, respectively, and a dye-sensitized solar cell produced using bis-ZnP are shown in FIG. 5 and FIG. 6 (current-voltage curve), FIG. 7 and FIG. 8 (action spectrum), FIG. 9 and FIG. 10 (current-voltage curve in the dark), and Table 1. The evaluation conditions were as follows: electrode area: 0.25 cm$^2$, incident light intensity: 1 sun (AM: 1.5, 100 mW cm$^{-2}$, with mask). Incidentally, FIGS. 5 to 10 and Table 1 also show the results of the evaluation of the cell performance of a dye-sensitized solar cell produced using ZnP as a comparative example. As is clear from FIGS. 5 to 10 and Table 1, it was found that when a diarylamino group is introduced into a meso position of a porphyrin ring, energy conversion efficiency (η) is improved, and also that the degree of improvement is highest in mono-ZnP. An increase in short-circuit current density ($J_{SC}$) with the improvement of light collection ability was seen in all of cis-ZnP, trans-ZnP, mono-ZnP, and bis-ZnP, and the degree of increase was high in cis-ZnP, mono-ZnP, and bis-ZnP. Open-circuit voltage ($V_{OC}$) was slightly lower in cis-ZnP, trans-ZnP, and bis-ZnP than in ZnP, but was significantly higher in mono-ZnP than in ZnP. Fill factor (FF) was highest in mono-ZnP, but there was no big difference. Mono-ZnP was excellent in terms of the degree of suppression of charge recombination due to backward electron transfer in the dark. Consequently, mono-ZnP exhibited the highest cell performance.

TABLE 1

| | $J_{sc}$/mA cm$^{-2}$ | $V_{oc}$/V | FF | η/% |
|---|---|---|---|---|
| cis-ZnP | 13.0 | 0.64 | 0.67 | 5.5 |
| trans-ZnP | 10.7 | 0.64 | 0.65 | 4.4 |
| mono-ZnP | 13.1 | 0.72 | 0.69 | 6.5 |
| bis-ZnP | 13.4 | 0.63 | 0.67 | 5.7 |
| ZnP | 9.26 | 0.66 | 0.67 | 4.1 |

INDUSTRIAL APPLICABILITY

According to the invention, it is possible to provide a novel porphyrin complex having excellent light collection characteristics and a dye-sensitized solar cell using the porphyrin complex as a sensitizing dye. In this respect, the present invention is industrially applicable.

The invention claimed is:
1. A porphyrin complex comprising a porphyrin derivative and a metal atom, the porphyrin derivative having:
a carboxyaryl group, which is unsubstituted or is substituted on the aryl ring, attached to at least one of four meso positions of a porphyrin ring that is unsubstituted or substituted at the β-position; and
a diarylamino group, which is unsubstituted or is substituted on one or both of the aryl rings, attached to at least either of a meso position adjacent to or a meso position opposite to the meso position to which a carboxylaryl group is attached.

2. A porphyrin complex according to claim 1, represented by the following general formula (1):

[Chemical Formula]

(1)

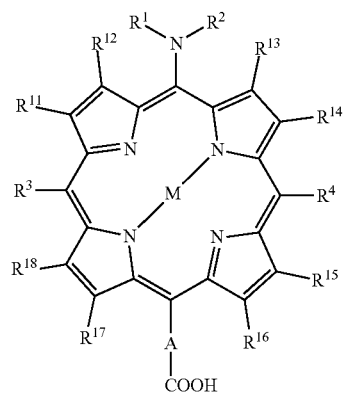

wherein
A represents an unsubstituted or substituted arylene group, $R^1$ and $R^2$ may be the same or different and each represent an optionally unsubstituted or substituted aryl group, $R^3$ and $R^4$ may be the same or different and each represent a diarylamino group unsubstituted or substituted on one or both of the aryl rings, a carboxyaryl group unsubstituted or substituted on the aryl ring, an unsubstituted or substituted aryl group, or an arylethynyl group unsubstituted or substituted on the aryl ring,
$R^{11}$ to $R^{18}$ may be the same or different and each represent a hydrogen atom, an unsubstituted or substituted alkyl group, an unsubstituted or substituted aryl group, an arylethynyl group unsubstituted or substituted on the aryl ring, or a halogen atom, and
M represents a metal atom.

3. A porphyrin complex according to claim 1, represented by the following general formula (2):

[Chemical Formula]

(2)

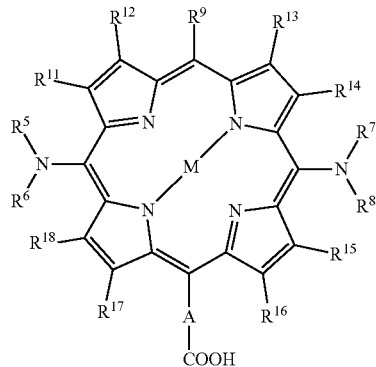

wherein
A represents an unsubstituted or substituted arylene group, $R^{11}$ to $R^{18}$ may be the same or different and each represent a hydrogen atom, an unsubstituted or substituted alkyl group, an unsubstituted or substituted aryl group, an arylethynyl group unsubstituted or substituted on the aryl ring, or a halogen atom,
M represents a metal atom,
$R^5$, $R^6$, $R^7$, and $R^8$ may be the same or different and each represent an unsubstituted or substituted aryl group, and
$R^9$ represents an unsubstituted or substituted aryl group or an arylethynyl group unsubstituted or substituted on the aryl ring.

4. A porphyrin complex according to claim 1, wherein the number of diarylamino groups attached is 2 or more.

5. A porphyrin complex according to claim 1, wherein the metal atom is Zn, Cu, Ti, Ni, Fe, or Mg.

* * * * *